United States Patent [19]

Doyle et al.

[11] Patent Number: 4,919,803
[45] Date of Patent: Apr. 24, 1990

[54] LIQUID CHROMATOGRAPHIC CHIRAL STATIONARY PHASE

[75] Inventors: Thomas D. Doyle, Burke; Charlotte A. Brunner, Alexandria, both of Va.; Edward Smith, Rockville, Md.

[73] Assignee: The United States of America as represented by the Secretary of the Department of Health and Human Services, Washington, D.C.

[21] Appl. No.: 281,778

[22] Filed: Dec. 9, 1988

[51] Int. Cl.$^5$ .............................................. B01D 15/08
[52] U.S. Cl. ........................... 210/198.2; 210/502.1; 210/635; 210/656; 502/401
[58] Field of Search ..................... 210/635, 656, 198.2, 210/502.1; 502/401, 402, 404

[56] References Cited

U.S. PATENT DOCUMENTS

| | | | |
|---|---|---|---|
| 4,290,893 | 9/1981 | Hare et al. | 210/656 |
| 4,318,819 | 3/1982 | Malloy et al. | 252/184 |
| 4,318,820 | 3/1982 | Malloy et al. | 252/184 |
| 4,322,310 | 3/1982 | House | 252/184 |
| 4,512,898 | 4/1985 | Oi et al. | 210/656 |
| 4,604,207 | 8/1986 | Oi et al. | 210/635 |
| 4,818,394 | 4/1989 | Okamoto | 210/656 |

*Primary Examiner*—Ernest G. Therkorn
*Attorney, Agent, or Firm*—Birch, Stewart, Kolasch & Birch

[57] ABSTRACT

A novel packing material for liquid chromatographic use is disclosed. This packing material is prepared by covalently bonding (S)- or (R)-6-methoxy-α-methyl-2-naphthaleneacetic acid (naproxen) to aminopropylsilanized silica. The resulting chiral stationary phase is effective for the resolution of enantiomeric (RS)-naproxen, and of other racemic α-methylarylacetic acids.

8 Claims, 1 Drawing Sheet

Resolution of Naproxen
(a) = (R)-naproxen
(b) = (S)-naproxen
Conditions as above Resolution of Naproxen
(a) = (R)-naproxen
(b) = (S)-naproxen
Conditions as above Resolution of Ibuprofen
(a) = (R)-ibuprofen
(b) = (S)-ibuprofen
Conditions as above

LIQUID CHROMATOGRAPHIC CHIRAL STATIONARY PHASE

FIELD OF THE INVENTION

The present invention relates to a packing material for chromatographic use, and a method for the resolution of racemic compounds using this packing material.

BACKGROUND OF THE INVENTION

U.S. Pat. Nos. 4,604,207 and 4,512,898 to Oi et al disclose packing materials for chromatographic use and a method for analysis of an enantiomer using such packing material. The packing material taught by U.S. Pat. No. 4,512,898 comprises an inorganic carrier having hydroxyl groups at the surface thereof having grafted thereon an organosilane derivative. The organosilane derivative can be a urea derivative obtained by reacting an optically active isocyanate with an aminoalkylsilane, an N-carbamoyl amino acid derivative obtained by reacting an optically active amino acid carbamoylated by isocyanate with an aminoalkylsilane and an O-carbamoyl hydroxy acid derivative obtained by reacting an optically active hydroxy acid carbamoylated by isocyanate with an aminoalkylsilane. This packing material is used as a stationary phase for liquid chromatography for separating and analyzing an enantiomer mixture of certain compounds. The packing material disclosed in U.S. Pat. No. 4,604,207 comprises an inorganic carrier having hydroxyl groups at the surface thereof having grafted thereon an α-arylalkylamine derivative. The α-arylalkylamine derivative is formed by bonding an optically active α-arylalkylamine with an aminoalkylsilane through a dibasic carboxylic acid. This packing material is also utilized as a stationary phase for liquid chromatographic analysis of an enantiomer mixture.

U.S. Pat. No. 4,322,310 is directed to chiral supports for the separation and resolution of racemates by chromatography. These chiral supports comprise a chiral organic amine covalently linked via a carbamate, mercaptocarbamate, or urea linkage to a chain of atoms whose other terminus is covalently bonded to a core support.

There are a variety of strategies for the construction of chiral stationary phases used in chromatographic applications. One of the most useful of these strategies involves the synthesis of stationary phases in which a relatively small chiral molecule is chemically bound to an inert support, and in which the chiral molecule so bound contains multiple-interaction sites. Specifically, these sites include (1) aromatic donor-acceptor, (2) hydrogen-bonding (or dipolar), and (3) bulky steric sites, all in proximity to the chiral center.

One theory pertinent to chromatographic separation and resolution of chiral molecules on such stationary phases was described by Pirkle. This theory postulates discrete and specific interactions between functional groups on the resolved chiral molecules (solutes) with discrete, specific and complementary groups on the chiral stationary phase (CSP). For example, if an aromatic pi-acidic group on the solute interacts with a pi-basic group on the CSP, a hydrogen-bond donating group in the solute with a corresponding accepting group in the CSP, and a steric group in the solute with a similar group in the CSP, and if all of these interactions occur essentially simultaneously, then this theory postulates that this interaction results in a high likelihood of effective chiral discrimination, with consequent resolution of the enantiomeric solutes on the chromatographic stationary phase.

An important extension of this theory involves the inherent reciprocality between the chiral solutes and the chiral molecule bound to the stationary phase. The structural features of chiral solutes which make them good candidates for efficient chromatographic resolution are the same structural features which make them conceptually logical candidates as molecules which could be bound to inert supports, so as to serve thereby as new chiral stationary phases. This principle of reciprocality has seldom been explicitly and deliberately utilized for the design of new CSP's. The present invention represents a particularly straightforward, novel and successful application of this concept.

SUMMARY OF INVENTION

An object of the present invention is to provide a chromatographic packing material comprising a chiral stationary phase.

Another object of the present invention is to provide a liquid chromatography chiral stationary phase which is effective for the resolution of racemic α-methylarylacetic acids and similar non-steroidal anti-inflammatory pharmaceutical substances.

Still another object of the present invention is to provide a method for the efficient liquid chromatographic separation and resolution of racemic α-methylarylacetic acids and similar non-steroidal anti-inflammatory pharmaceutical substances.

Yet another object of the invention is to provide a liquid chromatographic packing material which will not lose its efficiency or enantioselectivity over several months of continuous use.

A further object of the present invention is to prepare a chiral stationary phase by bonding (R)- or (S)-6-methoxy-α-methyl-2-naphthaleneacetic acid to aminopropylsilanized silica, which can be used to resolve racemic 6-methoxy-α-methyl-2-naphthaleneacetic acid.

These and other objects are accomplished by providing a packing material for chromotographic analysis which comprises a chiral stationary phase (CSP) formed from a silica support bonded to (R)- or (S)-naproxen via an amide linkage. Racemic 6-methoxy-α-methyl-2-napthaleneacetic acid (naproxen) has the following formula:

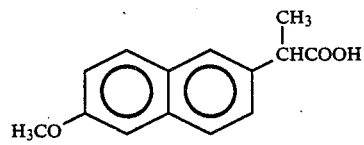

(S)-naproxen has the following formula:

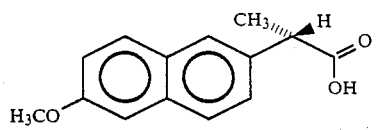

(R)-naproxen has the following formula:

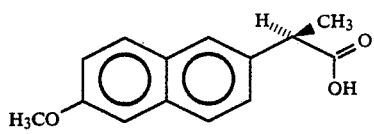

The naproxen enantiomer is bonded to a support via an amide linkage so as to form the chiral stationary phase. Thus, if (S) or (R)-naproxen is covalently bonded to aminopropylsilanized silica, the resultant chiral stationary phases would have the following respective formulas:

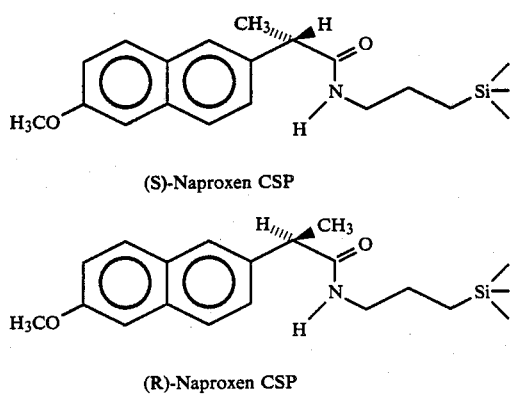

There is also provided a method for the chromatographic resolution of racemic α-methylarylacetic acid compounds. This method comprises passing the racemic α-methylarylacetic acid compound through a liquid chromatograph having a packing material as described above. In one preferred embodiment, the method is particularly effective for the liquid chromatographic resolution of the enantiomeric 3,5-dinitroanilide of (RS)-6-methoxy-α-methyl-2-naphthaleneacetic acid (racemic naproxen). Other racemic α-methylarylacetic acid compounds which can be effectively resolved by the present CSP include α-methyl-4-(2-methylpropyl)-benzeneacetic acid (ibuprofen), α-methyl-3-phenoxybenzeneacetic acid (fenoprofen), 3-benzoyl-α-methylbenzeneacetic acid (ketoprofen), α-methyl-4-(2-thienylcarbonyl) benzeneacetic acid (suprofen), 6-chloro-α-methyl-9H-carbazole-2-acetic acid (carprofen), 4-(1,3-dihydro-1-oxo-2H-isoindol-2-yl)-α-methylbenzeneacetic acid (indoprofen), 3-chloro-4-(2,5-dihydro-1H-pyrrol-1-yl)-α-methylbenzeneacetic acid (pirprofen), 2-(4-chlorophenyl)-α-methyl-5-benzoxazoleaceticacid (benoxaprofen), and 2-fluoro-α-methyl [1,1'-biphenyl]-4-acetic acid (flurbiprofen).

BRIEF DESCRIPTION OF THE DRAWINGS

The present invention will become more fully understood from the detailed description given hereinbelow and the accompanying drawings which are given by way of illustration only, and thus are not limitative of the present invention, and wherein.

DETAILED DESCRIPTION OF THE INVENTION

Figure 1:
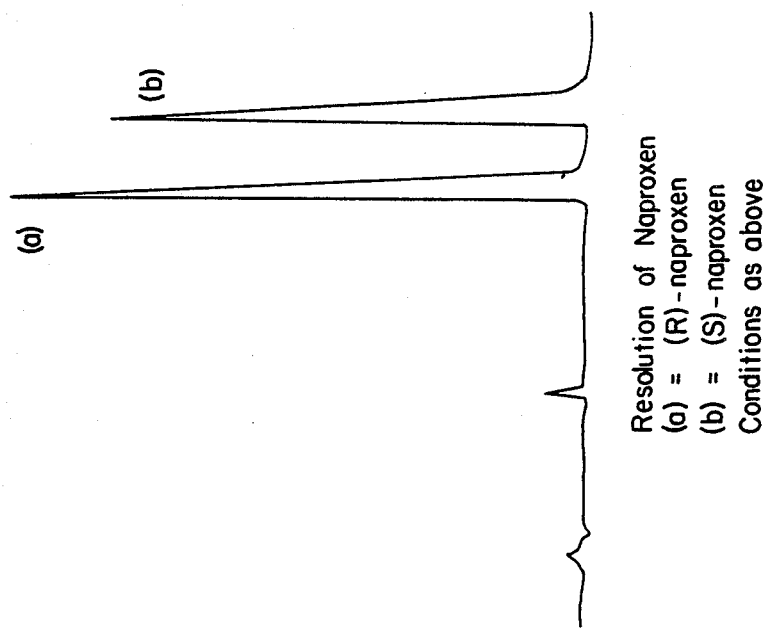
FIG. 1 is a chromatogram obtained from the resolution of naproxen using the present chiral stationary phase.

The present naproxen CSP is useful in many types of chromatography, including general liquid chromatography, high performance liquid chromatography (HPLC), thin-layer chromatography (TLC) in which the naproxen chiral moiety may be bound to, e.g., aminopropylsilanized silica forming a thin film on glass plates, and supercritical fluid chromatography (SCF), in which the stationary phase is the same as described previously, but the mobile phase is a carrier fluid under supercritical conditions. The present CSP is preferably used in HPLC.

Although the above presentation of the present invention shows (R)- or (S)-naproxen bonded to a support of aminopropylsilanized silica via an amide linkage, any support with pendant amino groups would be suitable for bonding to (R)- or (S)-naproxen via an amide linkage. For example, the pendant amino group attached to the silica support may include alkylamino, alkylpolyamino, or arylamino groups. Aminopropylsilanized silica is a well-known material widely available from a number of manufacturers, both in the form of prepacked columns or bulk material. If a prepacked column is used, the enantiomeric naproxen can easily be attached to the support by an in-situ reaction with the support. If a bulk material is used, the enantiomeric naproxen can be attached to the silica support outside the column, and then packed into columns by known techniques.

The packing material of the present invention can be prepared, for example, by covalently bonding (S)-naproxen (or (R)-naproxen) to n-aminopropylsilanized silica. N-ethoxycarbonyl-2-ethoxy-1,2-dihydroxyquinoline (EEDQ) is utilized (consumed) in the reaction scheme. EEDQ basically forms an intermediate with the (R)- or (S)-naproxen, and this intermediate then reacts with the n-aminopropylsilanized silica to ultimately produce the present CSP. Thus the function of the EEDQ is to serve as a "carboxyl activator". EEDQ reacts with naproxen in a 1:1 stoichiometric ratio. The resulting intermediate then reacts with the amino group of the column support, liberating carbon dioxide and ethanol. One mole of EEDQ is consumed in the reaction for each mole of naproxen bound to the support. The resulting chiral stationary phase consists of (S)-naproxen or (R)-naproxen chemically bonded to the silica by an amide linkage, and this structure is produced by the following basic reaction scheme:

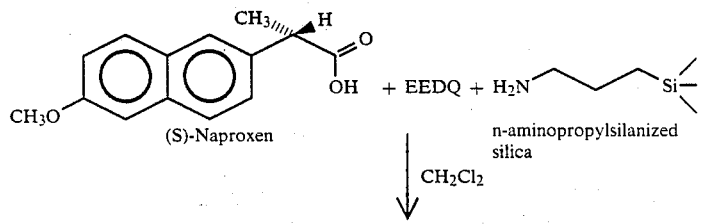

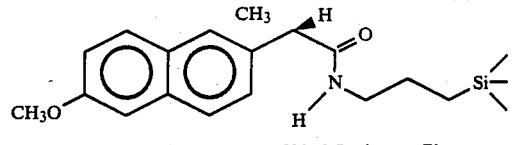

(S)-Naproxen Chiral Stationary Phase

The (S)-Naproxen Chiral Stationary Phase.

The (S)-Naproxen (or R-Naproxen) Chiral Stationary Phase can be prepared by a simple, one-step, in-situ procedure in a prepacked column, without the use of special and complicated equipment. Methylene chloride is the preferred solvent, but chloroform or any other suitable solvent may be used.

Naproxen is an important non-steroidal anti-inflammatory agent. It is commercially available as the (S)-enantiomer. One significant achievement of the present invention is its innovative use of the principle of reciprocality. The present invention permits one to use naproxen to resolve itself by chromatographic analysis. The essential concept is that chiral solutes, which are well resolved on chiral stationary phases, are themselves excellent candidates for the construction of such stationary phases, where they can serve as resolving centers. The present inventors' application of this concept resides in the recognition that naproxen has structural features that make it a good candidate both for chiral resolution as a solute, and, by application of the principle of reciprocity, for the construction of an effective CSP. In particular, the chemical structure of naproxen contains (1) a strongly pi-basic naphthyl group, (2) a polar carboxyl group, and (3) a moderately bulky methyl group, all directly attached to the chiral center.

Preparation of the Chiral Stationary Phase

A solution of 2.30 g (S)-naproxen and 2.47 g EEDQ in 100 ml methylene chloride was pumped at 2 ml/min through a 4.6×250 mm, 5 micron, aminopropyl silanized column (Bakerbond Amino ($NH_2$), stainless steel, J. T. Baker Co.). This solution was recycled through the column for four hours. The column was then washed by pumping through at 2 ml/min, successively, 100 ml methylene chloride, 60 ml methanol, 20 ml isopropanol, and then 10% isopropanol in hexane until the UV detector response at 254 nm was stable. The resulting (S)-naproxen chiral stationary phase is completely stable for use as an analytical HPLC column, under normal-phase conditions.

From the manufacturer's specifications and experimental results, the loading of naproxen on the column was determined to be 320 mg (1.4 mmole) (S)-naproxen on the 4.6×250 mm column, or 1.3 mg (0.0056 mmole) per mm cross-sectional length of column. The naproxen should be bound to the column support material in an amount sufficient to consume available amino groups, and to produce a satisfactory chromatographic separation.

Several different compounds were analyzed on this column having the prepared chiral stationary phase. Specific examples thereof are described below.

EXAMPLE 1

Racemic naproxen (to be used as the analytical sample) was first chemically derivatized by well-known standard methods with 3,5-dinitroaniline to form the 3,5-dinitroanilide. This derivatization with 3,5-dinitroaniline is known, and it is conducted to add a complementary pi-acidic aromatic group to the compound to be analyzed or resolved into its (R)- and (S)-enantomeric forms. This pi-acidic aromatic group can then interact through pi-pi bonding with the pi-basic naphthyl group of the CSP. Other pi-acidic groups may be used in place of the 3,5-dinitrophenyl group. Thionylchloride could be substituted for oxalyl chloride.

In a typical preparation, 20 mg of a mixture of (R)- and (S)-naproxen and 1 ml of oxalyl chloride (neat) were refluxed for fifteen minutes. Excess oxalyl chloride was then removed under vacuum at 30°–40° C., and the residue was redissolved in three successive portions of methylene chloride and the solvent removed under reduced pressure at 30° C. The resulting crude acid chloride of naproxen was dissolved in 2 ml of methylene chloride, 23 mg of 3,5-dintroaniline and 2 drops of triethylamine was added, and the mixture was allowed to stand for one hour. The solution was then diluted to 20 ml with methylene chloride, washed successively with 20 ml each of 0.1M NaOH, 1M HCl, and water, then dried with anhydrous sodium sulfate. The resulting solution of (RS)-naproxyl-3,5-dinitroanilide may be injected on the naproxen CSP directly or evaporated to dryness to obtain the solid derivative.

This 3,5-dinitroanilide of naproxen was then chromatographed on the (S)-naproxen chiral stationary phase prepared as described above, using a mobile phase consisting of hexane:isopropanol:acetonitrile (80:20:4), to resolve the enantiomeric (R)- and (S)-naproxen molecules. The flow rate was 0.5 ml/min. at a temperature of 20° C. The separation factor ($\alpha$) was 1.21 and the resolution factor ($R_s$) was 3.04. The number of theoretical plates averaged 6000. The elution order of the solutes was (R)-, (S)- on the (S)-CSP. FIG. 1 shows the chromatogram of the resolution.

EXAMPLE 2

Figure 2:
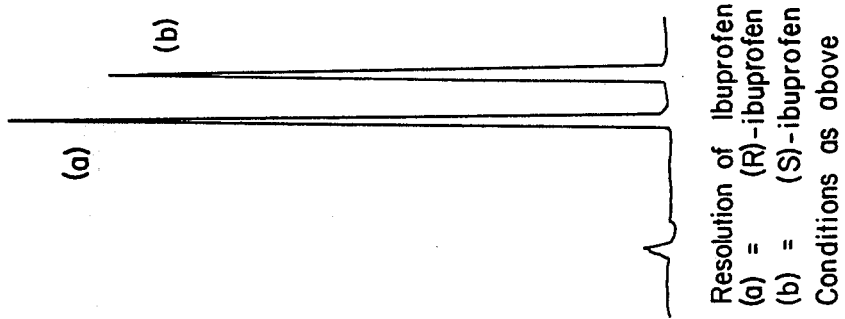
FIG. 2 is a chromatogram obtained from the resolution of ibuprofen using the present chiral stationary phase.

Racemic ibuprofen was converted to its 3,5-dinitroanilide form and then resolved in the same manner as described in Example 1, with the same mobile phase as in Example 1. The flow rate was 0.5 ml/min. at a temperature of 20° C. The number of theoretical plates averaged 7500. The elution order of the solutes was (R)-, (S)- on the (S)-CSP. FIG. 2 shows the chromatogram.

EXAMPLES 3–12

In accordance with the procedures described in Examples 1 and 2, the racemic compounds as shown in Table 1 were converted to their 3,5-dinitroanilide forms, and then resolved on the prepared S-naproxen CSP. The flow rate was 0.5 ml/min. at 20° C. The mobile phase was hexane:isopropanol (60:40). The results are shown in Table 1.

| Example No. | Compound | Capacity Factor, $k'_2$ | Separation Factor, $\alpha$ |
|---|---|---|---|
| 3 | naproxen | 6.70 | 1.23 |
| 4 | ibuprofen | 2.74 | 1.45 |

-continued

| Example No. | Compound | Capacity Factor, $k'_2$ | Separation Factor, $\alpha$ |
| --- | --- | --- | --- |
| 5 | fenoprofen | 5.00 | 1.26 |
| 6 | ketoprofen | 6.77 | 1.19 |
| 7 | suprofen | 10.03 | 1.16 |
| 8 | carprofen | 7.75 | 1.26 |
| 9 | indoprofen | 16.52 | 1.05 |
| 10 | pirprofen | 6.74 | 1.22 |
| 11 | benoxaprofen | 5.45 | 1.25 |
| 12 | flurbiprofen | 3.76 | 1.29 |

It is apparent from the principle of reciprocality that the (S)- and (R)-enantiomers of all the α-methylarylacetic acids shown to be resolved in Table 1 could themselves be bound to, for example, aminopropylsilanized silica, to form thereby new chiral stationary phases. Because all of the compounds in Table 1 have the general structure formula:

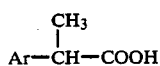

wherein Ar- is an aromatic group, it will be obvious that (S)- and (R)-chiral stationary phases can be constructed from these compounds in a manner exactly analogous to that used in the case of naproxen, to produce chiral stationary phases having the respective formulas shown below:

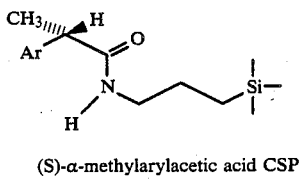

(S)-α-methylarylacetic acid CSP

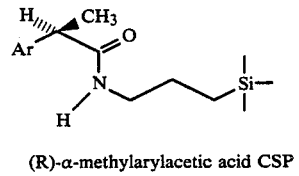

(R)-α-methylarylacetic acid CSP

These additional chiral stationary phases, like the naproxen CSP, can be formed from a silica support bonded to the (R)- or (S) form of an α-methylarylacetic acid via an amide linkage. They could be used in chromatography analysis in the same manner as the naproxen CSP, i.e. as a packing material for chromatographic analysis.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A packing material for chromatographic use which comprises a chiral stationary phase formed from a silica support bonded to the (R)- or (S)-form of 6-methoxy-α-methyl-2-napthaleneacetic acid via an amide linkage.

2. A packing material according to claim 1, wherein 6-methoxy-α-methyl-2-napthaleneacetic acid is in its (S)-enantomeric form.

3. A packing material according to claim 2, wherein said chiral stationary phase has the following formula:

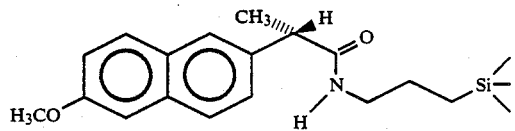

4. A packing material according to claim 1, wherein 6-methoxy-α-methyl-2-napthaleneacetic acid is in its (R)-enantomeric form.

5. A packing material according to claim 4, wherein said chiral stationary phase has the following formula:

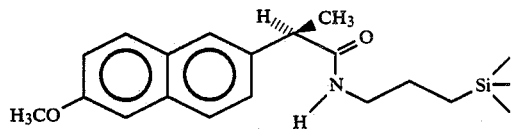

6. A packing material according to claim 1, wherein said silica support has pendant amino groups selected from the group consisting of alkylamino, alkylpolyamino, and arylamino.

7. A packing material according to claim 1, wherein said chromatographic use is selected from the group consisting of liquid chromatography, thin-layer chromatography, and supercritical fluid chromatography.

8. A packing material according to claim 7, wherein said liquid chromatography is high performance liquid chromatography.

* * * * *